US007910885B2

(12) United States Patent
Rosenberg et al.

(10) Patent No.: US 7,910,885 B2
(45) Date of Patent: Mar. 22, 2011

(54) SYSTEM AND METHOD FOR DETERMINING A CROSS SECTIONAL FEATURE OF A STRUCTURAL ELEMENT USING A REFERENCE STRUCTURAL ELEMENT

(75) Inventors: Zvika Rosenberg, Mevaseret Zion (IL); Ovadya Menadeva, Modiin (IL); Aviram Tam, Nes Ziona (IL)

(73) Assignee: Applied Materials Israel, Ltd., Rehovot (IL)

( * ) Notice: Subject to any disclaimer, the term of this patent is extended or adjusted under 35 U.S.C. 154(b) by 446 days.

(21) Appl. No.: 10/564,131

(22) PCT Filed: Jul. 12, 2004

(86) PCT No.: PCT/US2004/022347
§ 371 (c)(1),
(2), (4) Date: Oct. 26, 2006

(87) PCT Pub. No.: WO2005/008768
PCT Pub. Date: Jan. 27, 2005

(65) Prior Publication Data
US 2007/0051888 A1 Mar. 8, 2007

Related U.S. Application Data

(60) Provisional application No. 60/486,566, filed on Jul. 11, 2003.

(51) Int. Cl.
*G01N 23/00* (2006.01)
*G21K 7/00* (2006.01)
(52) U.S. Cl. .................. 250/310; 250/306; 250/307
(58) Field of Classification Search .............. 250/310, 250/311, 309, 306, 307, 492.2, 492.3
See application file for complete search history.

(56) References Cited

U.S. PATENT DOCUMENTS
5,161,201 A 11/1992 Kaga et al.
(Continued)

FOREIGN PATENT DOCUMENTS
EP 0 441 373 A2 8/1991
(Continued)

OTHER PUBLICATIONS

Applied Materials Israel, Ltd., International Search Report, PCT/US2004/022347, Sep. 2, 205, 7pp.

(Continued)

*Primary Examiner* — Robert Kim
*Assistant Examiner* — Brooke Purinton
(74) *Attorney, Agent, or Firm* — SNR Denton US LLP

(57) ABSTRACT

A system and method for determining a cross sectional feature of a measured structural element having a sub-micron cross section, the cross section is defined by an intermediate section that is located between a first and a second traverse sections. The method starts by a first step of scanning, at a first tilt state, a first portion of a reference structural element and at least the first traverse section of the measured structural element, to determine a first relationship between the reference structural element and the first traverse section. The first step is followed by a second step of scanning, at a second tilt state, a second portion of a reference structural element and at least the second traverse section of the measured structural element, to determine a second relationship between the reference structural element and the second traverse section. The method ends by a third step of determining a cross sectional feature of the measured structural element in response to the first and second relationships.

37 Claims, 11 Drawing Sheets

U.S. PATENT DOCUMENTS

| | | | |
|---|---|---|---|
| 5,283,736 A * | 2/1994 | Nagatsuka et al. | 382/131 |
| 6,079,256 A * | 6/2000 | Bareket | 250/307 |
| 6,566,897 B2 * | 5/2003 | Lo et al. | 250/492.2 |
| 6,570,157 B1 * | 5/2003 | Singh et al. | 250/311 |
| 7,027,636 B2 * | 4/2006 | Oh | 250/306 |
| 7,282,716 B2 * | 10/2007 | Prelewitz et al. | 250/370.08 |
| 2002/0179812 A1 | 12/2002 | Kochi et al. | |
| 2003/0010914 A1 * | 1/2003 | Takane et al. | 250/310 |
| 2003/0168594 A1 * | 9/2003 | Muckenhirn | 250/307 |

FOREIGN PATENT DOCUMENTS

| | | |
|---|---|---|
| JP | S61-138107 | 6/1986 |
| JP | 2002-270126 | 9/2002 |
| WO | WO 01/45136 A1 | 6/2001 |
| WO | WO 2004/008255 A2 | 1/2004 |
| WO | WO 2004/072631 A2 | 8/2004 |

OTHER PUBLICATIONS

Patent Abstracts of Japan, vol. 010, No. 322 (p. 511), Oct. 31, 1986 & JP 61 128114 A, Toshiba Corporation, Jun. 16, 1986, Abstract.

Applied Materials Israel, Ltd.; Chinese Application No. 200480025993.2; Office Action mailed Dec. 7, 2007, 7pp.

Applied Materials Israel, Ltd.; JP Application No. P2006-520256; Notice of Reasons for Rejection dated Apr. 13, 2010, 5pp.

Applied Materials Israel, Ltd.: PCT/US2004/022347 filed Jul. 12, 2004; International Preliminary Report on Patentability; International Bureau of WIPO; Jan. 16, 2006; 9pp.

* cited by examiner

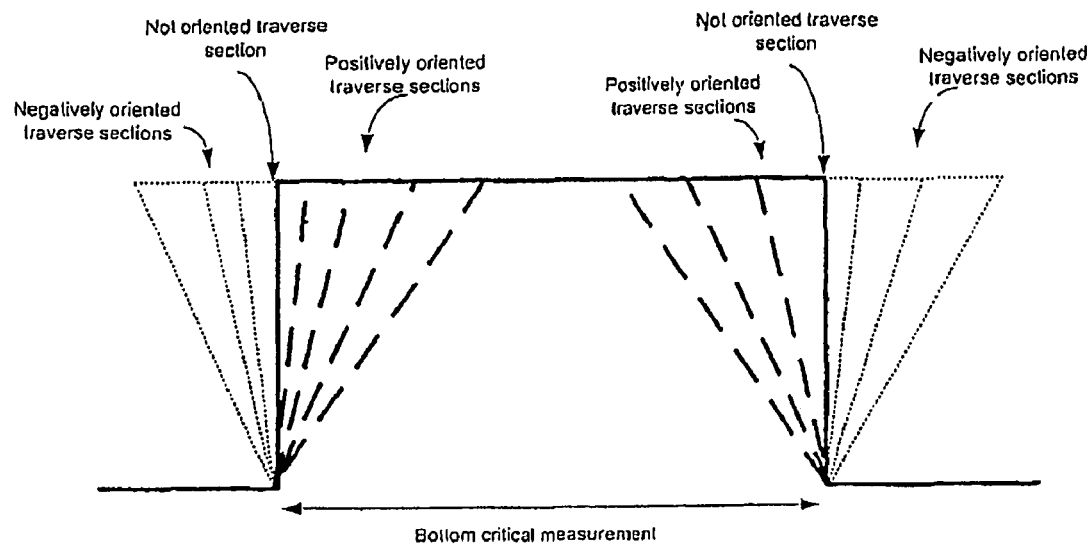
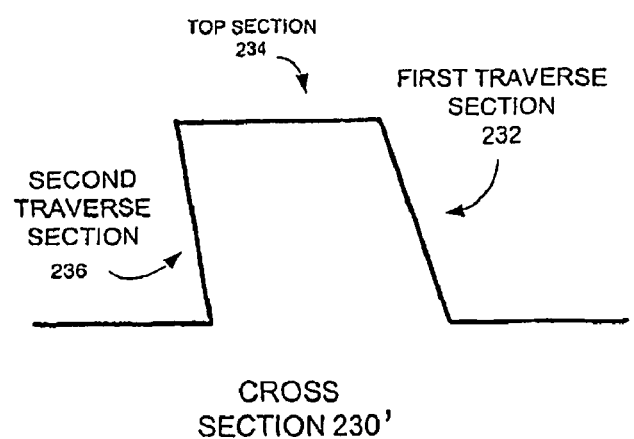
FIGURE 2b

400

470
Obtain a waveform representative of detection signals generated as a result of an interaction between a scanning electron beam and a structural element.

472
Calculate at least three points – a first point that is characterized by a maximal derivative value, a lower point and an upper point that are characterized by a predefined derivative values.

474
Determine a location point in response to an intersection between a height threshold and a line that is drawn between the upper and lower points.

520
Scanning, at a first tilt state, a first portion of a reference structural element and at least the first traverse section of the measured structural element, to determine a first relationship between the reference structural element and the first traverse section.

530
Scanning, at a second tilt state, a second portion of a reference structural element and at least the second traverse section of the measured structural element, to determine a second relationship between the reference structural element and the second traverse section.

540
Determining a cross sectional feature of the measured structural element in response to the first and second relationships.

Fig. 5

SYSTEM AND METHOD FOR DETERMINING A CROSS SECTIONAL FEATURE OF A STRUCTURAL ELEMENT USING A REFERENCE STRUCTURAL ELEMENT

CROSS REFERENCES TO RELATED APPLICATIONS

The present patent application is a national phase application of International Application No. PCT/US2004/022347 filed Jul. 14, 2004, which is a claims priority to U.S. Provisional Application No. 60/486,566 filed Jul. 11, 2003.

FIELD OF THE INVENTION

This invention relates to metrology systems and methods for determining features of sub-micron structural elements such as lines, contacts, trenches and the like, of measured objects such as, but not limited to, semiconductors wafers and reticles.

BACKGROUND OF THE INVENTION

Integrated circuits are very complex devices that include multiple layers. Each layer may include conductive material and isolating material, while other layers may include semi-conductive materials. These various materials are arranged in patterns, usually in accordance with the expected functionality of the integrated circuit. The patterns also reflect the manufacturing process of the integrated circuits.

Integrated circuits are manufactured by complex multi-staged manufacturing processes. During this multi-staged process, resistive material is (i) deposited on a substrate layer, (ii) exposed by a photolithographic process, and (iii) developed to produce a pattern that defines some areas to be later etched.

Various metrology, inspection and failure analysis techniques have evolved for inspecting integrated circuits both during the fabrication stages, between consecutive manufacturing stages, either in combination with the manufacturing process (also termed "in line" inspection techniques) or not (also termed "off line" inspection techniques). Various optical as well as charged particle beam inspection tools and review tools are known in the art, such as the VeraSEM™, ComPluss™ and SEM Vision™ of Applied Materials Inc. of Santa Clara, Calif.

Manufacturing failures may affect the electrical characteristics of the integrated circuits. Some of these failures result from unwanted deviations from the required dimensions of the patterns. A "critical dimension" is usually the width of a patterned line, the distance between two patterned lines, the width of a contact and the like.

One of the goals of metrology is to determine whether the inspected objects include deviations from these critical dimensions. This inspection is usually done by charged particle beam imaging that provides the high resolution required to measure said deviations.

A typical measured structural element is a line that has two opposing sidewalls. The measurement of the bottom width of the line involves measuring the top width of the line as well as measuring its sidewalls.

Measurement of a structural element line's critical dimensions using only a top view (in which the electron beam that scans the line is perpendicular to the substrate) may result in faulty results, especially when one of the sidewalls has a negative sidewall angle such that an upper end of the sidewall obscures a lower end of that sidewall.

In order to address said inaccuracies, CD-SEM tools that enable electronic tilt of an electron beam were introduced. NanoSem 3D, of Applied Materials from Santa Clara, is a fully automated CD-SEM that has a column that allows electronic tilting as well as mechanical tilting of the scanning electron beam to scan the wafer surface with various tilt angles from several directions.

Critical dimension measurement may involve illuminating a test object by multiple tilted beams and processing the detected waveforms to define critical dimensions.

Multiple measurements have some disadvantages. First, they reduce the throughput of the inspection system, especially when the measurement involves changing the tilt of the scanning electron beam. Such a change may require a de-Gauess stage, as well as an electron beam stabilization stage. A further disadvantage of multiple measurements results from degradation (for example shrinkage and carbonization) of the measured structural element, as well as unwanted charging of the measured structural element.

Due to various reasons, such as process variations, measurement inaccuracies and the like, the height and accordingly the measured height of structural elements varies across measured objects. In order to determine the structural height of a measured structural element, there is a need to perform at least two measurements of said structural element, at two different tilt angles. The height of the structural element may be estimated, usually in response to multiple height measurements of structural element across the measured object. The estimation may be associated with height measurement errors, as well as estimation errors, that can affect the critical dimension measurements.

SUMMARY OF THE INVENTION

The invention provides various scanning schemes that enable selectively reducing the amount of measurements required for determining cross sectional features of structural elements.

The invention provides methods and systems that allow accurate measurement of cross-dimensional features, with high accuracy, without knowing the height of the structural element.

The invention provides methods and systems that allow measurement of the whole cross-section of structural elements with a reduced number of scans and amount of measurements.

The invention provides a method for determining a cross sectional feature of a measured structural element having a sub-micron cross section, the cross section defined by an intermediate section that is located between a first and a second traverse sections. The method includes a first step of scanning a portion of at least one reference structural element and a portion of the measured structural element to determine one or more relationships between the at least one reference structural element and the measured structural element. The first scanning step may be followed by additional scanning steps. According to an embodiment of the invention, at least one additional scanning step is mandatory. According to other embodiments of the invention, one or more additional scanning steps are optional, and their execution may be responsive to a fulfillment of various conditions, such as an uncertainty associated with the results of the previous scan. The uncertainty may be related to a steepness or orientation of a portion of a section of a measured structural element, to a relationship between a width of a section of the measured element and to a width of an electron beam that scans that section. The conditions may also reflect the required signal to noise ratio of the measurement, the accuracy of the measurement, and, optionally or alternatively, to the topography of the measured object.

If additional scans are performed, additional relationships may be determined. Usually, the scans are performed at different scan states.

According to an aspect of the invention, one or more reference structural elements are provided. If multiple reference structural elements are provided, reference structural elements may be positioned on both sides of a measured structural element, but this is not necessarily so.

The invention provides a system for determining a cross sectional feature of a structural element having a sub-micron cross section, the cross section defined by an intermediate section that is located between first and second traverse sections, the system including means for directing an electron beam towards an inspected object, at least one detector that is positioned so as to detect electrons emitted from the beam; and a processor, coupled to the at least one detector. The system is capable of performing at least one measurement, at one or more tilt states, to determine one or more relationships between one or more structural elements and portions of a measured structural element. At least two relationships help to determine the cross sectional feature.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 2a-2b illustrate various lines and reference structural elements;

FIG. 4 is a flow chart of a method for determining an edge of a structural element having a sub-micron cross section, in accordance with an embodiment of the invention; and FIGS. 5-9 are flow charts of methods for determining a cross sectional feature of a measured structural element having a sub-micron cross section, the cross section defined by an intermediate section that is located between first and second traverse sections.

DETAILED DESCRIPTION OF THE DRAWINGS

A typical CD-SEM includes an electron gun, for generating an electron beam, deflection and tilt units as well as focusing lens, for enabling scanning of a specimen with an electron beam, that may be in a certain tilt condition, while reducing various aberrations and misalignments. Electrons, such as secondary electrons, emitted as result of an interaction between the specimen and the electron beam are attracted to a detector that provides detection signals which are subsequently processed by a processing unit. The detection signals may be used to determine various features of the specimen, as well as form images of the inspected specimen.

The invention may be implemented on CD-SEMs of various architectures that may differ from each other by the number of parts as well as the arrangement of said parts. For example the number of deflection units, as well as the exact structure of each unit may vary. The CD-SEM may include in-lens as well as out-of-lens detectors or a combination of both.

Figure 1A:
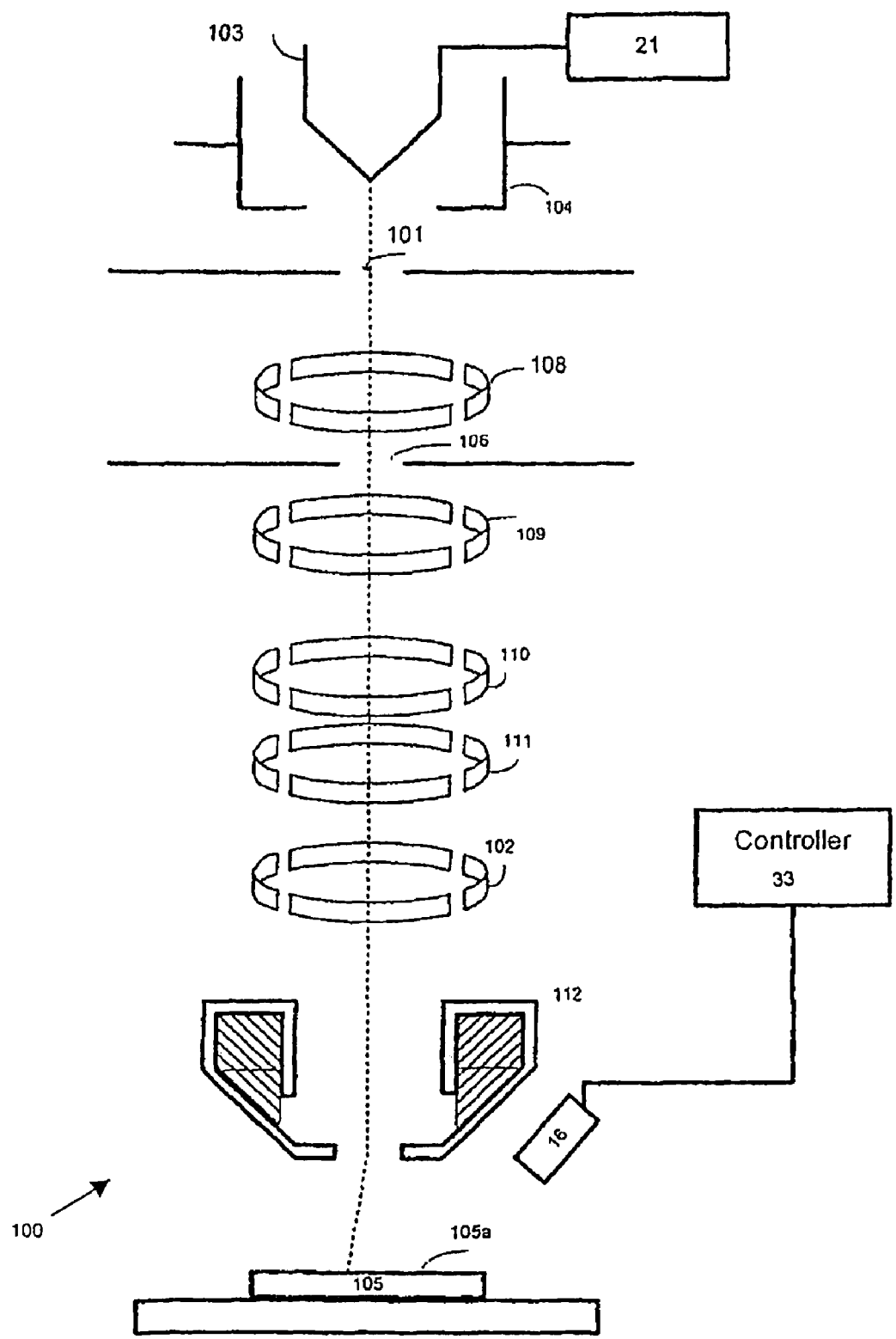
FIG. 1a is a schematic illustration of a critical dimension scanning electron microscope, in accordance with an embodiment of the invention.

A block diagram of a critical dimension scanning electron microscope (CD-SEM) 100 is shown schematically in FIG. 1a. CD-SEM 100 includes an electron gun 103 emitting an electron beam 101, which is extracted by the anode 104. The objective lens 112 focuses the electron beam on the specimen surface 105a. The beam is scanned over the specimen using the scanning deflection unit 102. An alignment of the beam to the aperture 106 or a desired optical axis respectively can be achieved by the deflection units 108 to 111. Instead of deflection unit coils, electrostatic modules in the form of charged plates or a combination of coils and electrostatic deflectors can be used.

In-lens detector 16 is able to detect secondary electrons that escape from the specimen 105 at a variety of angles with relatively low energy (3 to 50 eV). Measurements of scattered or secondary corpuscles from a specimen can be conducted with detectors in the form of scintillators connected to photomultiplier tubes or the like. Since the way of measuring the signals does not influence the inventive idea in general, this is not to be understood as limiting the invention. It is noted that the CD-SEM may include, additionally or alternatively, at least one out-of-lens detector.

Detection signals are processed by a processing unit (that may be a part of controller 33, but this is not necessarily so) that may have image processing capabilities and is able to process the detection signals in various manners. A typical processing scheme includes generating a waveform that reflects the amplitude of the detection signal versus the scan direction. The waveform is further processed to determine locations of at least one edge, and other cross sectional features of inspected structural elements.

The different parts of the system are connected to corresponding supply units (such as high voltage supply unit 21) that are controlled by various control units, most of them omitted from the figure for simplifying the explanation. The control units may determine the current supplied to a certain part, as well as the voltage.

CD-SEM 100 includes a double deflection system that includes deflection units 110 and 111. Thus, the beam tilt introduced in the first deflection unit 110, can be corrected for in the second deflection unit 111. Due to this double deflection system, the electron beam can be shifted in one direction without introducing a beam tilt of the electron beam with respect to the optical axis.

Figure 1B:
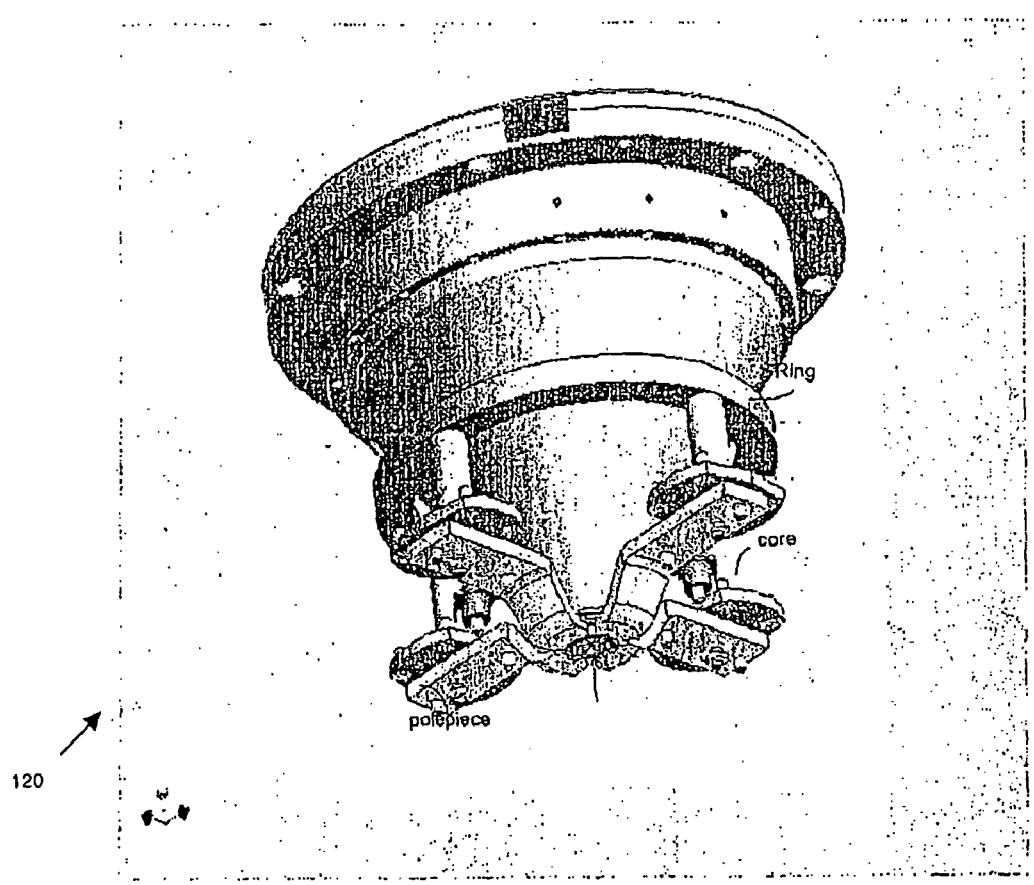
FIG. 1b is a perspective view of an objective lens, according to another embodiment of the invention.

FIG. 1b is a perspective view of an objective lens 120, according to another embodiment of the invention. In FIG. 1b, the tilt deflection is performed below (downstream direction) of the objective lens. Objective lens differs from objective lens 112 by having a pole-piece arranged in a quadrupole formation, positioned between the objective lens and specimen, for controlling the tilt condition of the electron beam. The polepieces are electrically connected to a ring and a core that bears additional coils (not shown) that are arranged so as to concentrate a magnetic flux in the space between the polepieces, through which the electron beam passes.

Modern CD-SEMs are able to measure structural elements that have cross sections that have sub-micron dimensions, with an accuracy of several nanometers. The size of these cross sections is expected to reduce in the future, as manufacturing and inspection processes continue to improve.

Various features of the cross section may be of interest. These features may include, for example, the shape of the cross section, the shape of one or more sections of the cross section, the width and/or height and/or angular orientation of the cross section sections, as well as the relationship between cross section sections. The feature can reflect typical values, as well as maximal and/or minimal values. Typically the width of the bottom of a line is of interest, but this is not necessarily so, and other features may be of interest.

Figure 2A:
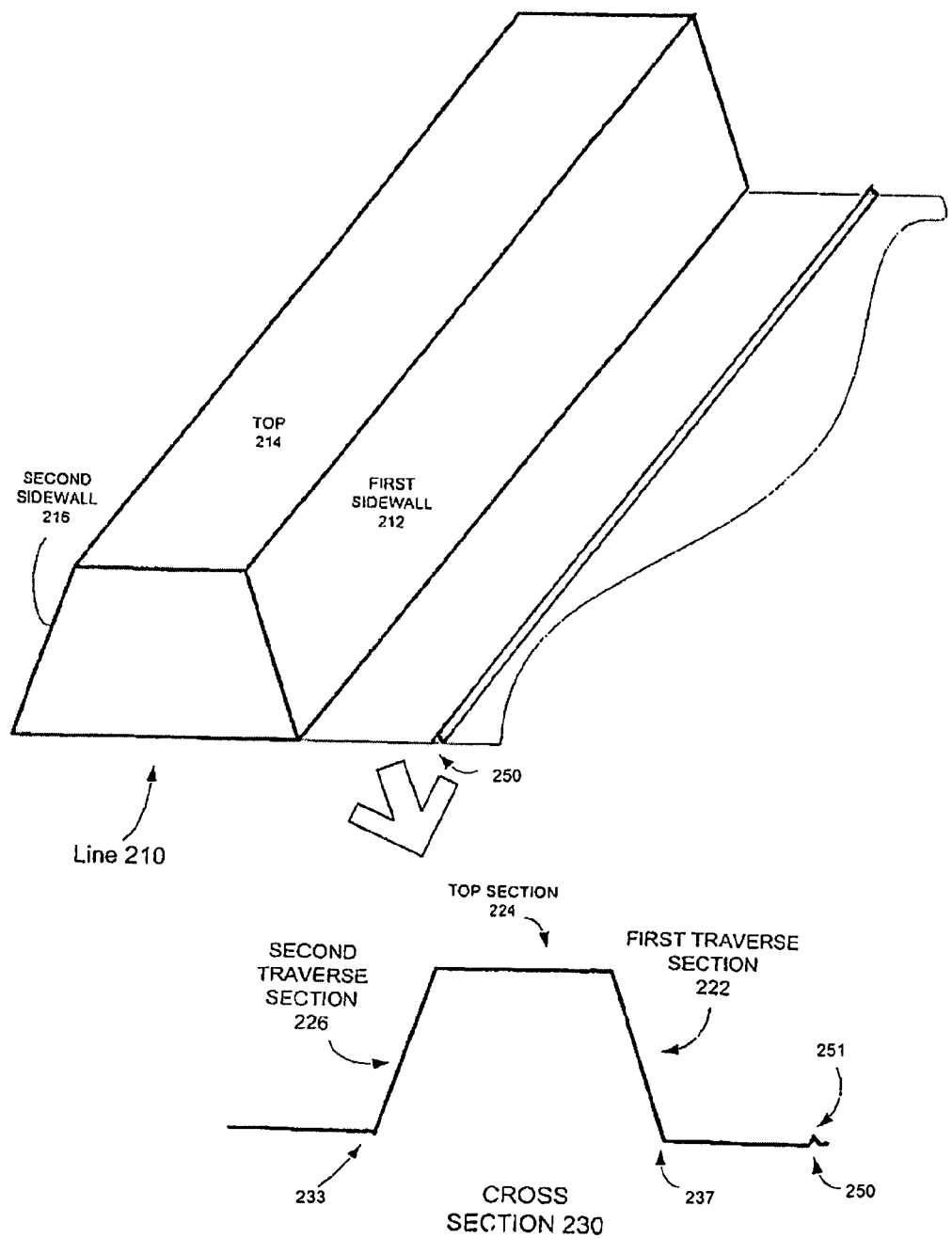

FIG. 2a illustrates a perspective as well as a cross sectional view of line 210 and a reference structural element, such as bump 250. Line 210 has a cross section 230 that includes a top section 224 and two substantially opposing traverse sections 222 and 226 (that correspond to the top section 214 as well as to two sidewalls 212 and 216 of line 210) that are both positively oriented at substantially opposing angles, such that the bottom of the line is not obscured by the top section 214.

Bump 250 is much smaller than line 210 and has at least one point, such as certain point 251, that is located substantially at the same plane as the lower points 233 and 237 of first and second traverse sections 222 and 226. Bump 250 is located so as to be viewed by electron beams that are used to scan the first traverse section as well as electron beams used to scan the second traverse section. The location of bump 250, and especially the relationship between its height (which is usually much smaller than the height of line 210) and the distance between bump 250 and line 210 are calculated to allow the bump 250 to be viewed by both types of electron beams. The distance can be responsive to the maximal tilt angle of the scanning electron beam. As a rule of thumb, the distance between bump 250 and line 210 has to be greater than $H_{max} \times \tangent(A_{max})$, in which $H_{max}$ is the maximal height of line 210 and $A_{max}$ is the maximal tilt angle of a scanning electron beam.

The inventors found that a bump can be generated relatively quickly using a charged electron beam that interacts with an object to provide a bump based upon the carbonization phenomena. For example, the inventors generated a 0.5 micron long carbonization line in less than a minute. Very good results were achieved by generating the bump by scanning the object multiple times (such as, but not limited to 10-50 scans) with a relatively low current electron beam (such as, but not limited to 20, 50, 100pA and the like). The inventors also found that such bumps can be achieved by using various acceleration voltages, in particular using 200v provided better results than using 500v or 1000v. Longer bumps usually required to increase the number of scans. It is noted that inaccuracies of the bumps can reflect the accuracy of the critical dimension measurements. The inventors found that the added error is less than 1 nano-meter, and that using several bumps and averaging the results for all bumps may improve the precision of the measurement.

FIG. 2b illustrates a cross section 230' of another line (not depicted) that has a top section 234, a first traverse section 232 that is positively oriented and a negatively oriented second traverse section 236. FIG. 2b also illustrates the convention of positive angles, negative angles and zero angle.

In some cases, a line may be positioned between first and second reference structural elements (e.g., two bumps similar to bump 250). The distance between the reference structural elements may be measured by performing multiple scans of said reference structural elements.

The inventors found that using reference elements that are positioned at opposing sides of a measured structural element may be useful in various cases, such as when a single structural element cannot be viewed by electron beams that scan the measured structural element from both of its sides. This can occur when other structural elements are positioned in a very close proximity to the measured structural element, such as to obscure the reference structural element.

Thus, in a dense array of lines 210, reference structural elements (e.g., bump 250) may be positioned between pairs of lines 210.

In other embodiments of the invention, multiple reference structural elements are positioned in proximity to a measured structural element, so as to allow multiple measurements of the relationship between the measured structural element and the multiple reference structural elements and to allow statistical processing of the multiple relationships to provide better results. Said statistical processing may average out or otherwise reduce errors and/or inaccuracies associated with a single measurement. This may result from an increment of the overall signal to noise ratio. In some cases, an array of reference structural elements (e.g., similar to bump 250) may be positioned at a first side of a line (e.g., similar to line 210), while in other cases, an array of reference structural elements may be positioned on both sides of a measured structural element. The bottom CD of a line can be responsive to multiple distances measured with respect to these reference structural elements.

It is noted that although the above discussion refers to line shaped measured structural elements and reference structural elements, the method and system are applicable to determine cross sectional features (such as top CD, bottom CD, maximal CD, and the like) of various structural elements, such as contacts, recesses and the like. The reference structural elements may have other shapes.

Figure 3A:
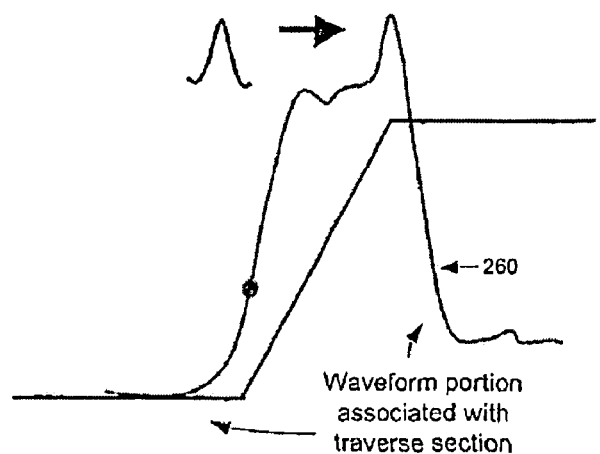
FIGS. 3a-3c are schematic illustrations of waveforms that represent a relatively wide positively oriented traverse section, a relatively narrow traverse section and a negative oriented traverse section.
Figure 3B:
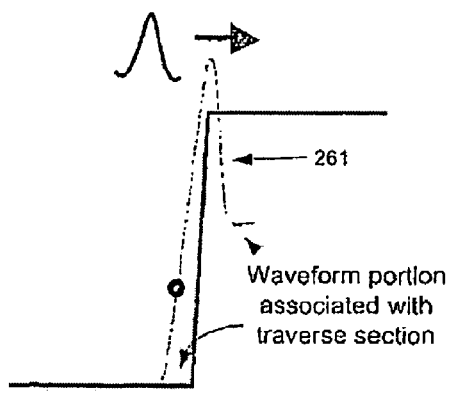
Figure 3C:
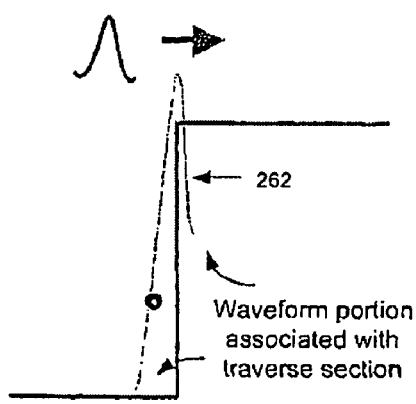

FIGS. 3a-3c are schematic illustrations of waveforms 260-262 that represent a relatively wide positively oriented traverse section, a relatively narrow traverse section and a negative oriented traverse section respectively. As can be seen from these figures, the waveform portion associated with steep sidewalls, as well as negative oriented sidewalls is relatively narrow and corresponds to the width of the scanning electron beam.

FIG. 4 illustrates a method 400 for determining a location of a traverse section. When a waveform is obtained from scanning a structural element, such as a line, by an electron beam, a portion of a derivative of this waveform may be obtained. For example, a waveform used to provide an estimate of the measure of a traverse section may include 3 points. An intermediate point has a maximal derivative value. The intermediate point is located between an upper point and a lower point, each associated with lower derivative values. The inventors have used an upper point that has a derivative value of about 80% of the maximal derivative value, and a lower point that has a derivative value of about 30% of the maximal derivative value, but other values can be used. A linear estimate of the traverse section is drawn between the upper and lower points. The intersection between said linear estimate and a height threshold provides a location point of the traverse section. The inventors used a height threshold of 35% of the maximal height of waveform 410, but other values can be used.

Referring to FIG. 4, method 400 starts by step 470 of obtaining a waveform, said waveform representative of detection signals generated as a result of an interaction between a scanning electron beam and a structural element.

Step 470 is followed by step 472 of calculating at least three points—a first point that is characterized by a maximal derivative value, and a lower point and an upper point that are characterized by a predefined derivative values.

Step 472 is followed by step 474 of determining a location point in response to an intersection between a height threshold and a line that is drawn between the upper and lower points.

According to an embodiment of the invention, the relationship between a reference structural element and a traverse section is actually the relationship between a certain point of the reference structural element and a location point of that traverse section. The certain point of the reference structural element may also be a location point.

It is noted that other points, such as an upper point, an intermediate point, a lower point and/or other points of waveforms 260-262 may be used in determining a relationship between a traverse section and a reference structural element.

FIG. 5 is a flow chart of method 500 for determining a cross sectional feature of a measured structural element having a sub-micron cross section, the cross section defined by an intermediate section located between first and second traverse sections.

Method 500 measures a feature of a structural element. The measured structural element is a part of a measured object, such as a wafer, die or dice. If appropriate reference structural elements are not positioned at the vicinity of the measured element, they may be added by use of prior art methods for adding and/or removing material, such as Focused Ion Beam (FIB) based methods, electron beam or even laser based methods. These methods may also require the provision/injection of gas/plasma in a manner known in the art. A system that implements some of these techniques is the SEM Vision G2 FIB of Applied Materials Inc. of Santa Clara, Calif.

Method 500 starts at step 520 of scanning, at a first tilt state, a first portion of a reference structural element and at least the first traverse section of the measured structural element, to determine a first relationship between the reference structural element and the first traverse section.

Conveniently, the first relationship is a distance between a certain point of the reference structural element and a first edge of the first traverse section. As illustrated by FIG. 2a, method 500 can be responsive to the relationship between a measured structural element and a single reference structural element, but may be responsive to additional relationships between the measured structural element and multiple reference structural elements.

Conveniently, the bottom of the measured structural element and the certain point of the reference structural element are substantially located on the same plane. Usually the height of the reference structural element, and especially the height of a certain reference point, is much smaller than a height of the measured structural element.

It is noted that the invention can be adapted to handle other shaped and/or sized structural elements. The height of the reference structural element may be taken into account, for example by using elementary geometrical equation to compensate for a height difference between the bottom of the measured structural element and the reference structural element.

Step 520 is followed by step 530 of scanning, at a second tilt state, a second portion of a reference structural element and at least the second traverse section of the measured structural element, to determine a second relationship between the reference structural element and the second traverse section.

Step 530 is followed by step 540 of determining a cross sectional feature of the measured structural element in response to the first and second relationships.

According to another embodiment of the invention, if one or more additional relationships were determined during steps 520 and 530, then the determination of step 540 is further responsive to at least one of the additional relationships.

It is noted that during a tilt stage the electron beam may be tilted in relation to an imaginary plane that is perpendicular to the measured object. The tilt angle can be positive or negative. According to an embodiment of the invention, during the first tilt state the electron beam is tilted at a positive angle, while during the second tilt state the electron beam is tilted at a negative angle.

According to another embodiment of the invention, during the first tilt state the electron beam is tilted at a negative angle, while during the second tilt state the electron beam is tilted at a positive angle.

According to an embodiment of the invention, during the first or second tilt state the electron beam is tilted at substantially zero degrees.

It is noted that large tilt angles, such as 15 degrees and even more, can be achieved by using prior art tools such as the NanoSem 3D or the VERASem of Applied Materials Inc.

Figure 6:
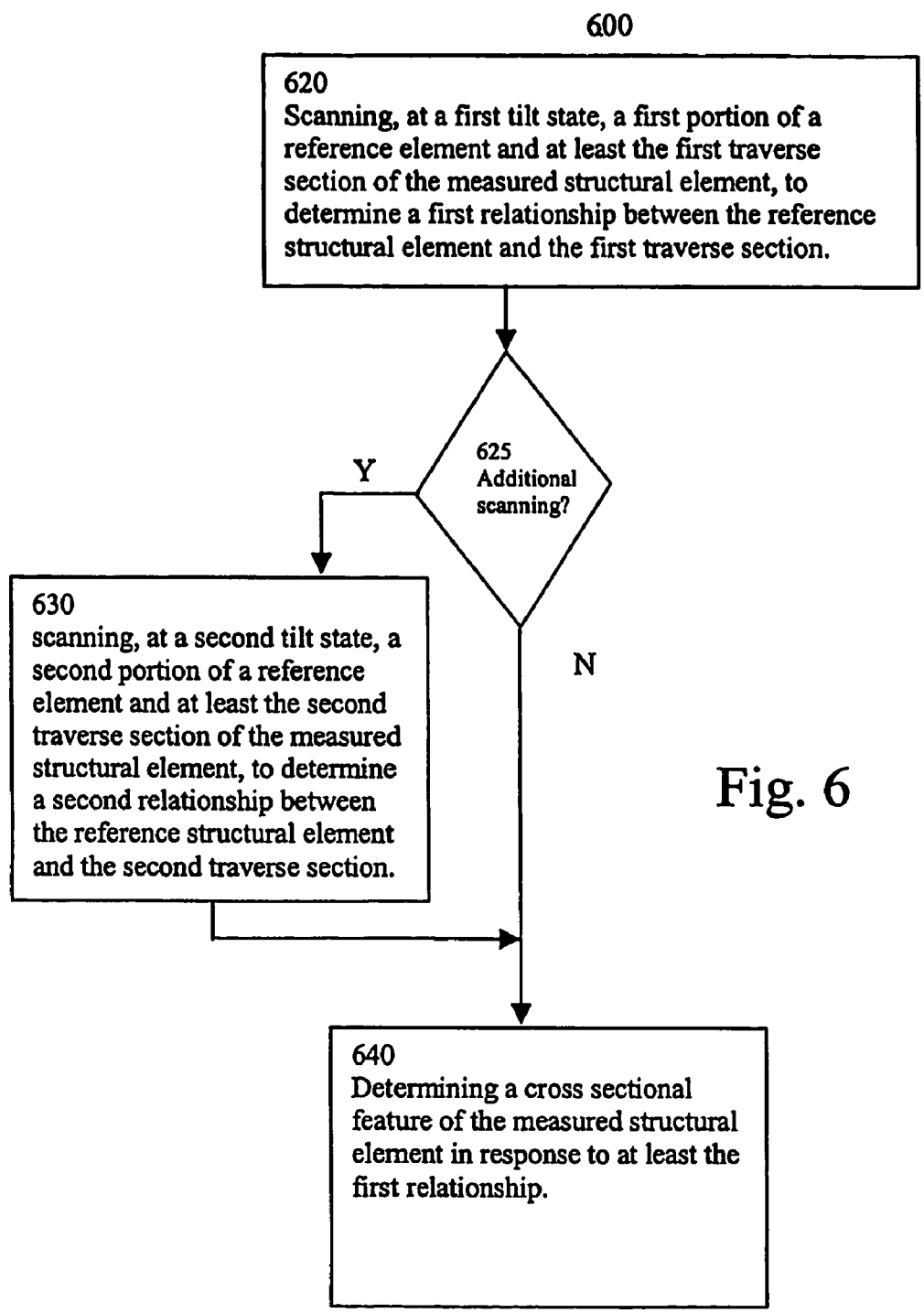

FIG. 6 is a flow chart of method 600 for determining a cross sectional feature of a measured structural element having a sub-micron cross section, the cross section defined by an intermediate section located between first and second traverse sections.

Method 600 starts by step 620 of scanning, at a first tilt state, a first portion of a reference element and at least the first traverse section of the measured structural element, to determine a first relationship between the reference structural element and the first traverse section.

Step 620 is followed by query step 625 of determining whether to perform an additional scanning step. If the answer is yes, method 600 proceeds to step 630, else the method proceeds to step 640.

The determination of step 625 may be responsive to various parameters, such as, but not limited to, top, bottom, maximal and/or minimal width of the measured structural element, estimated or measured orientation of a traverse section and/or estimated or measured width of a traverse section. The estimation can involve processing of detection signals and comparison with detection signals originating from other structural elements. The comparison may involve die to die comparison, die to data base comparison and the like.

An additional scanning step may be required if one traverse section (or both) is (are) suspected to be either steep (for example above a steepness threshold) or to be negatively oriented. This orientation may be estimated from waveforms acquired during the detection of signals resulting from the scan of the measured structural element. Steep traverse sections, as well as negative oriented traverse sections, are associated with certain waveforms. The inventors found that such traverse sections are suspected if the width of the waveform substantially equals the width of the electron beam. The inventors also found that a comparison of waveforms to previously recorded waveforms of known elements may also be used.

Step 630 includes scanning, at a second tilt state, a second portion of a reference element and at least the second traverse section of the measured structural element, to determine a second relationship between the reference structural element and the second traverse section.

Step 630 is followed by step 640 of determining a cross sectional feature of the measured structural element in response to at least the first relationship.

According to another embodiment of the invention, if one or more additional relationships were determined during steps 620 and 630, then the determination of step 640 is further responsive to at least one of the additional relationships.

Figure 7:
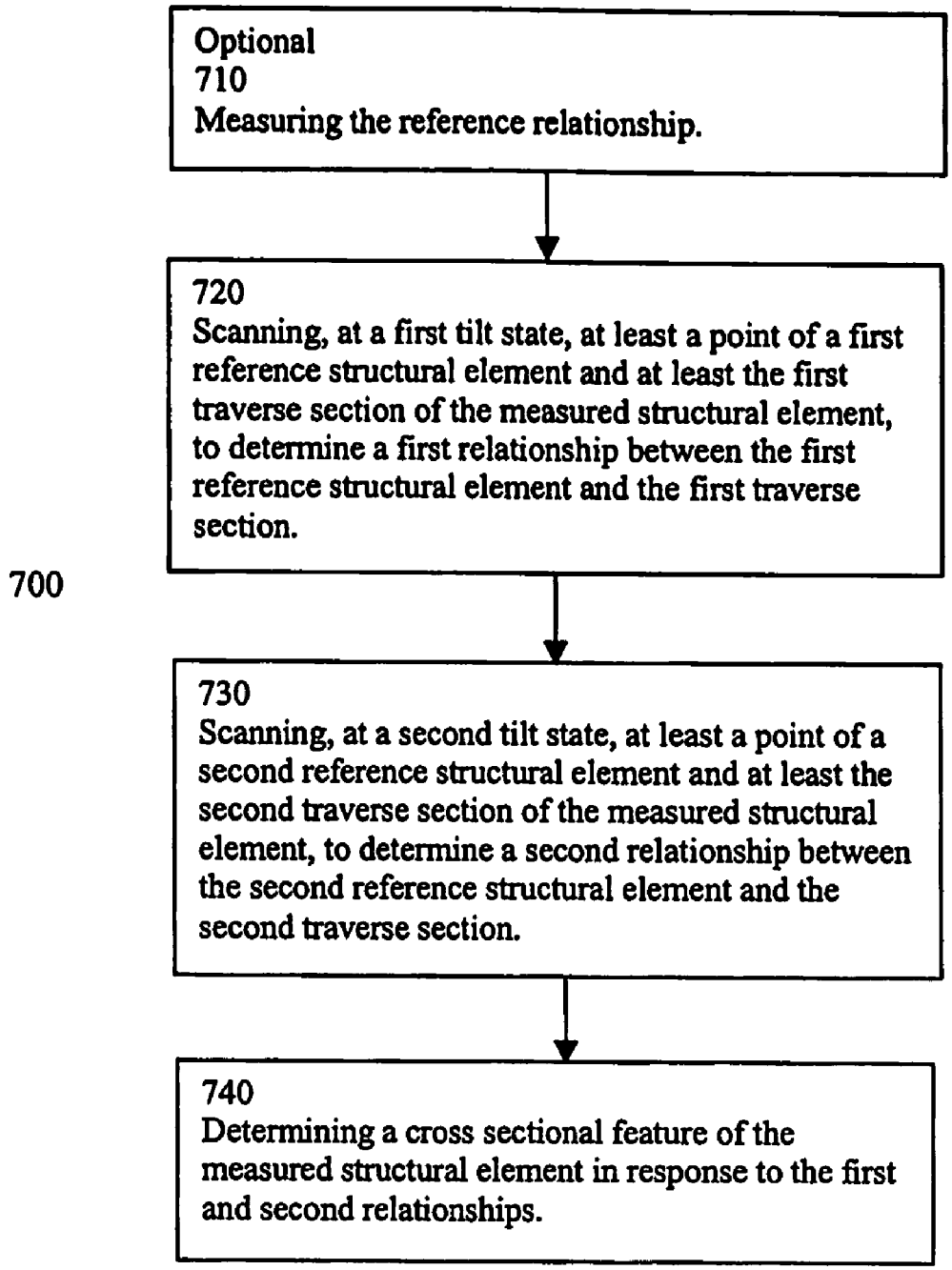

FIG. 7 is a flow chart of method 700 for determining a cross sectional feature of a measured structural element having a sub-micron cross section, the cross section defined by an intermediate section located between a first and a second traverse sections.

Method 700 starts at step 720 of scanning, at a first tilt state, at least a point of a first reference structural element and at least the first traverse section of the measured structural element, to determine a first relationship between the first reference structural element and the first traverse section.

Step 720 is followed by step 730 of scanning, at a second tilt state, at least a point of a second reference structural element and at least the second traverse section of the measured structural element, to determine a second relationship between the second reference structural element and the second traverse section.

Step 730 is followed by step 740 of determining a cross sectional feature of the measured structural element in response to the first and second relationships.

According to an embodiment of the invention, the measured structural element is positioned between the first and second reference structural elements.

The relationship (usually distance and optionally height difference) between the first and second reference elements must be measured/ estimated. Inaccuracies in this measurement may affect the measurement of the cross sectional feature.

Step 700 may include a preliminary step of either estimating or receiving this reference relationship, but it may also include a step 710 of measuring it. The measurement may take place in locations other than the location in which the measured element is being measured, so that various contamination, carbonization or shrinkage effects will not affect the measurement of the measured structural element.

Step 710 may include one or more scans of an area that includes the first and second points of the first and second reference elements and the measured structural element. Step 710 may also include preventing the electron beam from illuminating the measured structural element. This can be implemented by blanking the beam while it is supposed to illuminate the measured structural element.

Figure 8:
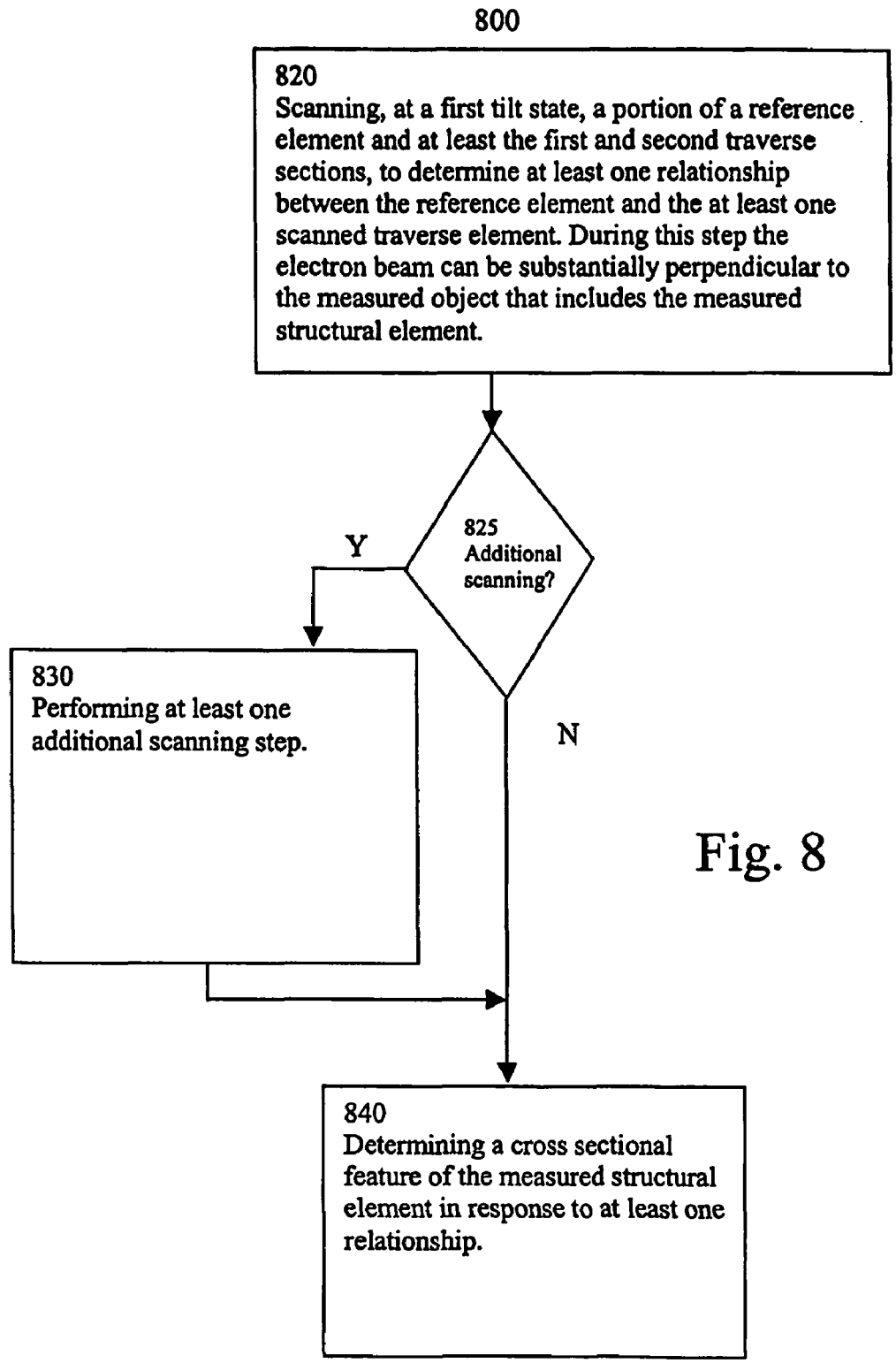

FIG. 8 is a flow chart of method 800 for determining a cross sectional feature of a measured structural element having a sub-micron cross section, the cross section defined by an intermediate section located between a first and a second traverse section.

Method 800 starts at step 820 of scanning, at a first tilt state, a portion of a reference element and at least the first and second traverse sections, to determine at least one relationship between the reference element and the at least one scanned traverse element. During this step the electron beam can be substantially perpendicular to the measured object that includes the measured structural element.

Step 820 is followed by query step 825 for determining whether an additional scanning step is required for determining an additional relationship between the reference structural element and the at least one traverse section. If the answer is positive, method 820 proceeds to step 830, else it proceeds to step 840. This determination may be responsive to an estimated width of a traverse section, to an estimated orientation of a traverse section, to an estimated cross sectional feature of the measured structural element, and the like.

Step 830 includes performing at least one additional scanning step. Conveniently, the tilt state differs from the first tilt state of step 820.

Step 840 involves determining a cross sectional feature of the measured structural element in response to at least one relationship.

Figure 9:
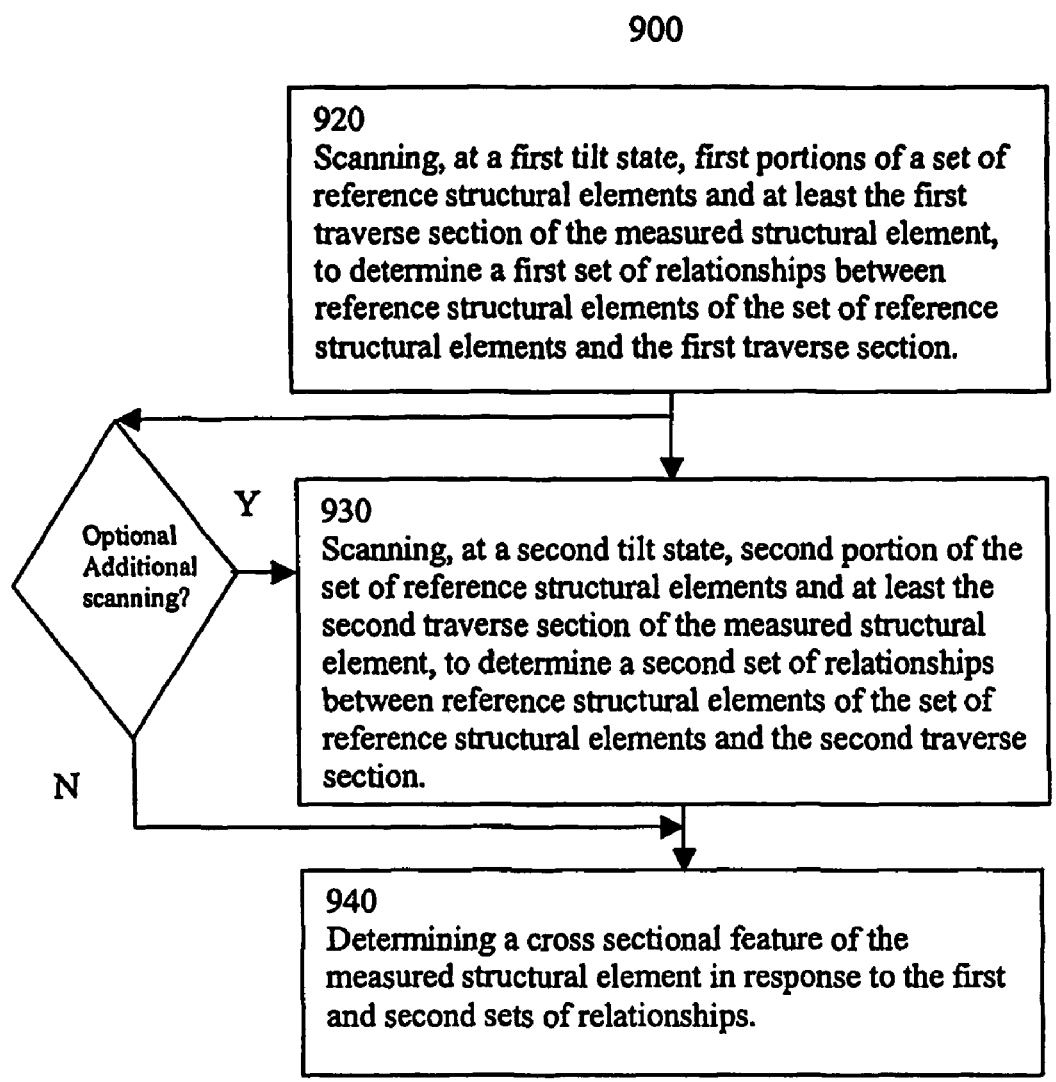

FIG. 9 is a flow chart of method 900 for determining a cross sectional feature of a measured structural element having a sub-micron cross section, the cross section defined by an intermediate section located between a first and a second traverse sections.

Method 900 starts by step 920 of scanning, at a first tilt state, first portions of a set of reference structural elements and at least the first traverse section of the measured structural element, to determine a first set of relationships between reference structural elements of the set of reference structural elements and the first traverse section.

Step 920 is followed by step 930 of scanning, at a second tilt state, second portions of the set of reference structural elements and at least the second traverse section of the measured structural element, to determine a second set of relationships between reference structural elements of the set of reference structural elements and the second traverse section.

Step 930 is followed by step 940 of determining a cross sectional feature of the measured structural element in response to the first and second sets of relationships. Step 940 may include statistical processing of the relationships of the first set to provide a first relationship. It may also include statistical processing of the relationships of the second set to provide a second relationship.

According to another embodiment of the invention, method 900 may include a query step for determining a necessity of additional scanning steps, in addition to step 920, and to determine whether step 930 (or even additional scanning steps) is required.

Is noted that the intermediate section, which may be a top section in the case of an elevated structural element, may be determined from each of the scanning steps. It is further noted that given the first and second traverse section cross sectional features the cross section of the structural element as well as any feature (such as, but not limited to, top CD, bottom CD, maximal CD) of said cross section can be determined. A typical cross sectional feature is the horizontal projection of a traverse section. In cases where the tilt angle is relatively small, it is assumed that the tilt angle is approximately equal to the tangent of this angle.

It is noted that some of the measurements may be repeated, and that additional tilted scans of the structural element (with the same and/or differing tilt angles) may be performed for various reasons, such as averaging out statistical noise, and the like. Accordingly, methods 400 and 500 may include multiple measurements of one or more cross sectional features, even if the height of the structural elements were known or estimated and even if a certain cross sectional feature were measured.

The present invention can be practiced by employing conventional tools, methodology and components. Accordingly, the details of such tools, component and methodology are not set forth herein in detail. In the previous descriptions, numerous specific details are set forth, such as shapes of cross sections of typical lines, number of deflection units, etc., in order to provide a thorough understanding of the present invention. However, it should be recognized that the present invention might be practiced without resorting to the details specifically set forth.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

We claim:

1. A method for determining a cross sectional dimension of a measured structural element having a sub-micron cross section, the cross sectional dimension defining an intermediate section of the measured structural element that is located between first and second traverse sections of the measured structural element, the method comprising the steps of:
scanning, while an inspection tool is in a first tilt state, a reference structural element and at least the first traverse section of the measured structural element, to determine a first distance between a certain point of the reference structural element and the first traverse section, wherein the first traverse section represents a first edge of the measured structural element;
determining whether additional scanning is required based on one or more of an estimated width of the first traverse section and an estimated width of the second traverse section;
if the additional scanning is required, scanning, while the inspection tool is in a second tilt state, the reference structural element and at least the second traverse section of the measured structural element, to determine a second distance between the certain point of the reference structural element and the second traverse section, wherein the second traverse section represents a second edge of the measured structural element; and
determining a cross sectional dimension of the intermediate section of the measured structural element in response to at least the first distance, wherein the cross sectional dimension is located between the first and second traverse sections of the measured structural element.

2. The method of claim 1 wherein the first edge of the measured structural element and the certain point of the reference structural element are substantially located on a same plane.

3. The method of claim 1 wherein a height of the certain point of the reference structural element is much smaller than a height of the measured structural element.

4. The method of claim 1 further comprising a preliminary step of generating the reference structural element at a vicinity of the measured structural element.

5. The method of claim 1 wherein during the scanning, while the inspection tool is in the first tilt stage, a measurement angle defined between a measured object that includes the measured structural element and an electron beam that scans the measured structural element is substantially ninety degrees.

6. The method of claim 1 wherein at least one additional reference structural element is provided at a vicinity of the reference structural element and wherein the steps of scanning further comprise scanning the at least one additional reference structural element to provide at least a third distance, in addition to the first and second distances, between the at least one additional reference structural element and a traverse section of the measured structural element.

7. The method of claim 6 wherein the step of determining is further responsive to the third distance.

8. The method of claim 1 wherein performing the scanning, while the inspection tool is in the second tilt state, is in response to determining a feature of the first traverse section.

9. The method of claim 8 wherein the feature is the estimated width or an estimated orientation of the first traverse section.

10. The method of claim 9 wherein the orientation is estimated by comparing detection signals generated as a result of a scan of the first traverse section and detection signals generated as a result of at least one scan of another traverse section of known width.

11. The method of claim 1 wherein at least one additional reference structural element is provided at a vicinity of the reference structural element and wherein the steps of scanning further comprise scanning the at least one additional reference structural element to provide at least a third distance, in addition to the first and second distances, between the at least one additional reference structural element and a traverse section of the measured structural element.

12. The method of claim 11 wherein the step of determining the cross sectional dimension is further responsive to the third distance.

13. A method for determining a cross sectional dimension of a measured structural element having a sub-micron cross section, the cross sectional dimension defining an intermediate section of the measured structural element that is located between first and second traverse sections of the measured structural element, the method comprising the steps of:
scanning, while an inspection tool is in a first tilt state, at least a first point of a first reference structural element and at least the first traverse section of the measured structural element, to determine a first distance between the first reference structural element and the first traverse section, wherein the first traverse section represents a first edge of the measured structural element;
determining whether additional scanning is required based on one or more of an estimated width of the first traverse section and an estimated width of the second traverse section;
if the additional scanning is required, scanning, while the inspection tool is in a second tilt state, at least a second point of a second reference structural element and at least the second traverse section of the measured structural element, to determine a second distance between the second reference structural element and the second traverse section, wherein the second traverse section represents a second edge of the measured structural element; and
determining a cross sectional dimension of the intermediate section of the measured structural element in response to at least the first distance, wherein the cross sectional dimension is located between the first and second traverse sections of the measured structural element.

14. The method of claim 13 wherein the measured structural element is positioned between the first and second reference structural elements.

15. The method of claim 13 further comprising a step of measuring a distance between the first and second points.

16. The method of claim 15 wherein the measured structural element is positioned between the first and second reference structural elements and wherein the step of measuring the distance comprises performing at least one scan of the first and second points and the measured structural element.

17. The method of claim 16 wherein the at least one scan comprises preventing an electron beam from illuminating the measured structural element.

18. The method of claim 13 wherein the measured structural element is a line that has a top section and two substantially opposing sidewalls.

19. The method of claim 13 wherein the measured structural element is a contact.

20. The method of claim 13 wherein the measured structural element is a recess.

21. The method of claim 13 wherein at least one additional reference structural element is provided at a vicinity of the first and second reference structural elements and wherein the steps of scanning further comprise scanning the at least one additional reference structural element to provide a third distance, in addition to the first and second distances, between the at least one additional reference structural element and a traverse section of the measured structural element.

22. The method of claim 21 wherein the step of determining the cross sectional dimension is further responsive to the third distance.

23. The method of claim 13 wherein the scanning, while the inspection tool is in the first tilt stage, comprises scanning with an electron beam that is substantially perpendicular to a measured object that includes the measured structural element.

24. The method of claim 13 wherein the determination of whether additional scanning is required is further based on an estimated orientation of a traverse section.

25. The method of claim 13 wherein the determination of whether additional scanning is required is further based on an estimated cross sectional dimension of the measured structural element.

26. The method of claim 13 wherein the determination of whether additional scanning is required is further based on relationship between a threshold and an estimated cross sectional dimension of the measured structural element.

27. The method of claim 26 wherein the threshold is a maximal width of the measured structural element.

28. The method of claim 26 wherein the threshold is a minimal width of the measured structural element.

29. The method of claim 13 wherein at least one additional reference structural element is provided at a vicinity of the first and second reference structural elements and wherein the steps of scanning further comprise scanning the at least one additional reference structural element to provide a third distance, in addition to the first and second distances, between the at least one additional reference structural element and a traverse section of the measured structural element.

30. The method of claim 29 wherein the step of determining the cross sectional dimension is further responsive to the third distance.

31. A method for determining a cross sectional dimension of a measured structural element having a sub-micron cross section, the cross sectional dimension defining an intermediate section of the measured structural element that is located between first and second traverse sections of the measured structural element, the method comprising the steps of:
scanning, while an inspection tool is in a first tilt state, first portions of a set of reference structural elements and at least the first traverse section of the measured structural element, to determine a first set of distances between first certain points of reference structural elements of the set of reference structural elements and the first traverse section, wherein the first traverse section represents a first edge of the measured structural element;
determining whether additional scanning is required based on one or more of an estimated width of the first traverse section and an estimated width of the second traverse section,
if the additional scanning is required, scanning, while the inspection tool is in a second tilt state, second portions of the set of reference structural elements and at least the second traverse section of the measured structural element, to determine a second set of distances between second certain points of reference structural elements of the set of reference structural elements and the second traverse section, wherein the second traverse section represents a second edge of the measured structural element; and
determining a cross sectional dimension of the intermediate section of the measured structural element in response to at least the first set of distances, wherein the cross sectional dimension is located between the first and second traverse sections of the measured structural element.

32. The method of claim 31 wherein the step of determining comprises statistical processing of the distances of the first set to provide a first distance.

33. The method of claim 31 wherein the step of determining comprises statistical processing of the distances of the second set to provide a second distance.

34. The method of claim 31 wherein the set of reference structural elements is positioned at both sides of the measured structural element.

35. The method of claim 31 wherein the set of reference structural elements is positioned at one side of the measured structural element.

36. A system for determining a cross sectional dimension of a structural element having a sub-micron cross section, the cross sectional dimension defining an intermediate section that is located between first and second traverse sections of the structural element, wherein the first traverse section represents a first edge of the measured structural element and the second traverse section represents a second edge of the measured structural element, the system comprising:
means for directing an electron beam towards an inspected object including the measured structural element so as to scan, at a first tilt state, a reference structural element and at least the first traverse section of the structural element, and to scan at a second tilt state, the reference structural element and at least the second traverse section of the structural element;
at least one detector that is positioned so as to detect electrons emitted from the measured structural element as a result of an interaction with the electron beam; and
a processor, coupled to the at least one detector and to the directing means so as to process detection signals received from the at least one detector and to:
determine whether additional scanning after the scan at the first tilt state is required based on one or more of an estimated width of the first traverse section and an estimated width of the second traverse section;
determine a first distance between a certain point of the reference.structural element and the first traverse section;
if scanning at the second tilt state is performed, determine a second distance between the certain point of the reference structural element and the second traverse section; and
determine a cross sectional dimension of the intermediate section of the measured structural element in response to at least the first distance, wherein the cross sectional dimension is located between the first and second traverse sections of the measured structural element.

37. The system of claim 36 wherein the processor is capable of determining the cross sectional dimension in response to additional distances between the measured structural element and additional reference structural elements.

* * * * *